United States Patent
Cornish et al.

(12) 
(10) Patent No.: US 6,390,993 B1
(45) Date of Patent: May 21, 2002

(54) GUIDEWIRE HAVING LINEAR CHANGE IN STIFFNESS

(75) Inventors: Wayne E. Cornish, Oceanside; John Schreiner, Hemet; James Jacobs, Mountain View; Marc M. Jalisi, Temecula; Mark Richardson, Escondido, all of CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 09/203,140

(22) Filed: Dec. 1, 1998

Related U.S. Application Data

(63) Continuation-in-part of application No. 08/868,764, filed on Jun. 4, 1997.

(51) Int. Cl.[7] .................................................. A61B 5/00
(52) U.S. Cl. ...................................... 600/585; 604/525
(58) Field of Search ................................. 600/585, 433, 600/439; 604/95, 96, 280, 281

(56) References Cited

U.S. PATENT DOCUMENTS

| | | | |
|---|---|---|---|
| 4,538,622 A | 9/1985 | Samson et al. ............. 128/772 |
| 4,721,117 A * | 1/1988 | Mar et al. ................... 600/585 |
| 4,748,986 A | 6/1988 | Morrison et al. ........... 128/772 |
| 4,846,186 A * | 7/1989 | Box et al. ................... 600/585 |
| 4,955,384 A | 9/1990 | Taylor et al. ............... 128/772 |
| 4,991,602 A | 2/1991 | Amplatz et al. ............ 128/772 |
| 5,061,273 A | 10/1991 | Yock .......................... 606/194 |
| 5,120,308 A * | 6/1992 | Hess ............................. 604/95 |
| 5,135,503 A | 8/1992 | Abrams ....................... 604/164 |
| 5,341,818 A | 8/1994 | Abrams et al. ............. 128/772 |
| 5,380,307 A | 1/1995 | Chee et al. ................. 604/264 |
| 5,497,783 A | 3/1996 | Urick et al. ................ 128/772 |
| 5,516,336 A | 5/1996 | McInnes et al. ............ 606/194 |
| 5,636,641 A | 6/1997 | Fariabi ....................... 128/772 |
| 5,702,419 A * | 12/1997 | Berry et al. ................ 606/198 |
| 5,746,701 A | 5/1998 | Noone ......................... 600/585 |

FOREIGN PATENT DOCUMENTS

| | | |
|---|---|---|
| EP | 0597341 A1 | 5/1994 |
| EP | 0661073 A1 | 7/1995 |
| EP | 0744186 A1 | 11/1996 |
| EP | 0818251 A1 | 1/1998 |
| WO | WO 98/55173 | 12/1998 |

* cited by examiner

*Primary Examiner*—Eric F. Winakur
*Assistant Examiner*—Pamela L. Wingood
(74) *Attorney, Agent, or Firm*—Heller Ehrman White & McAuliffe LLP

(57) ABSTRACT

The invention is directed to a guidewire having a distal section with multiple distally tapered core segments with at least two contiguous distally tapering core segments in which the most distal tapered core segment preferably has a greater degree of taper than the proximally contiguous tapered core segment. The invention is also directed to an elongated intracorporeal device, preferably a guidewire or section thereof, that has a core member or the like with a plurality of contiguous tapered segments having taper angles that are configured to produce a linear change in stiffness over a longitudinal section of the device. The device may also have a core section with a continuously changing taper angle to produce a curvilinear profile that preferably is configured to produce a linear change in stiffness of the core over a longitudinal section of the device.

61 Claims, 9 Drawing Sheets

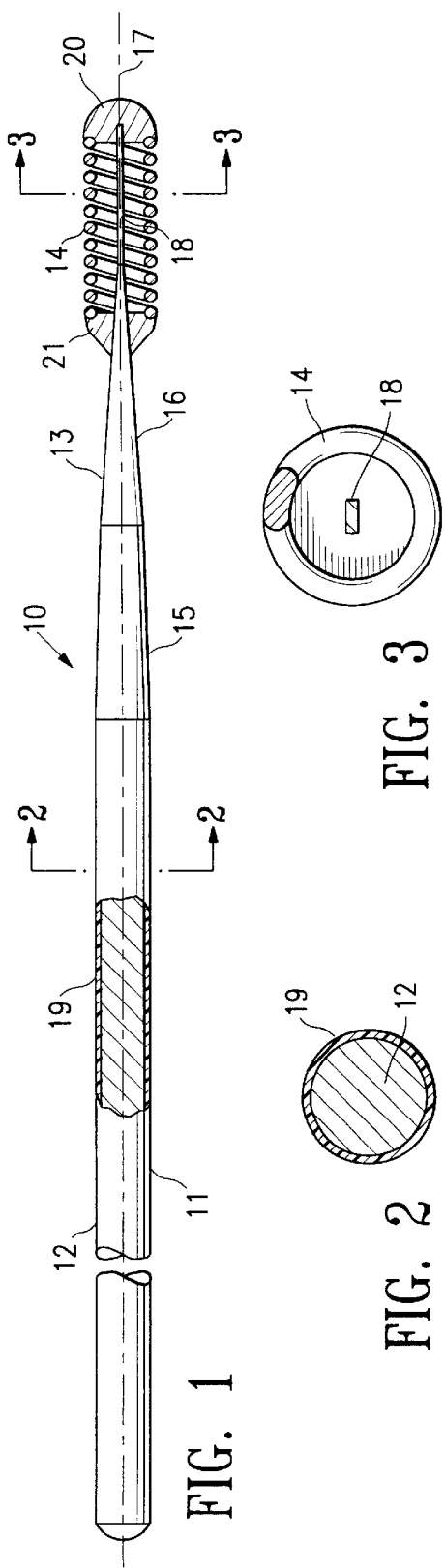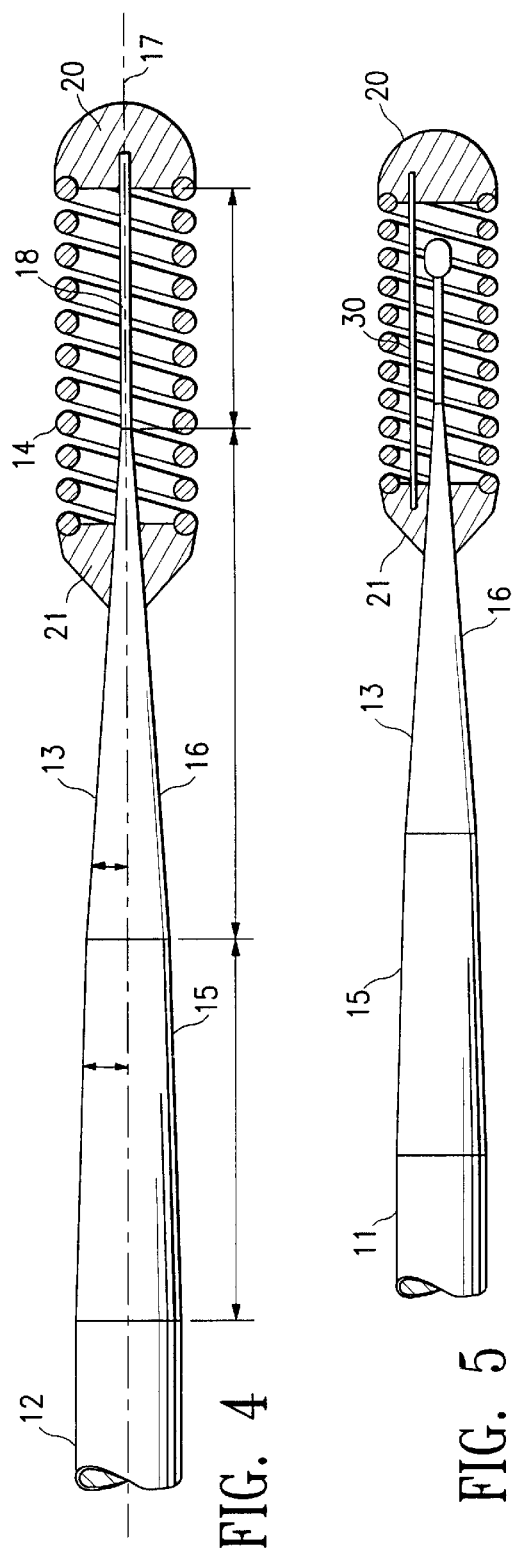

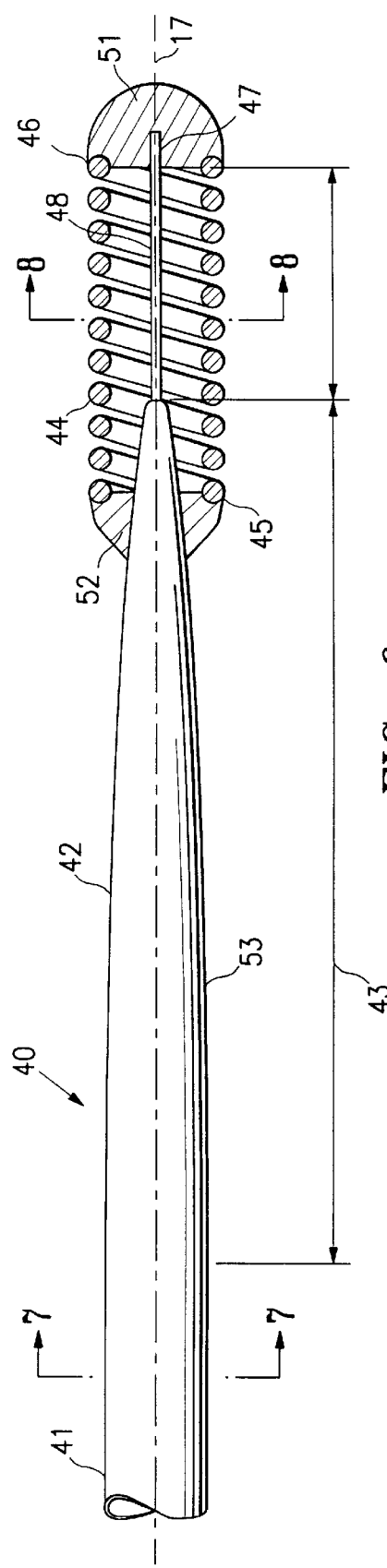
FIG. 8
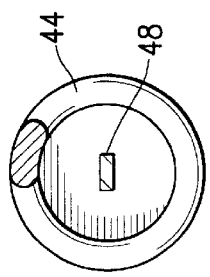
FIG. 7
FIG. 6

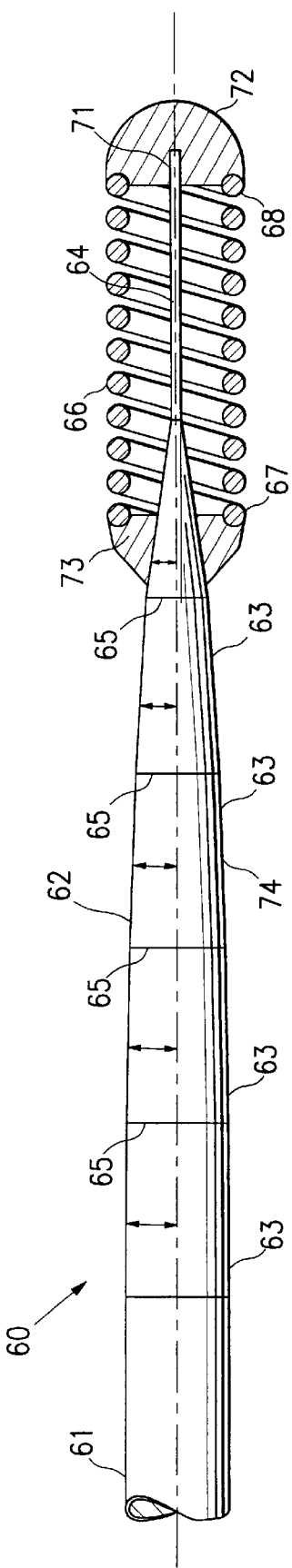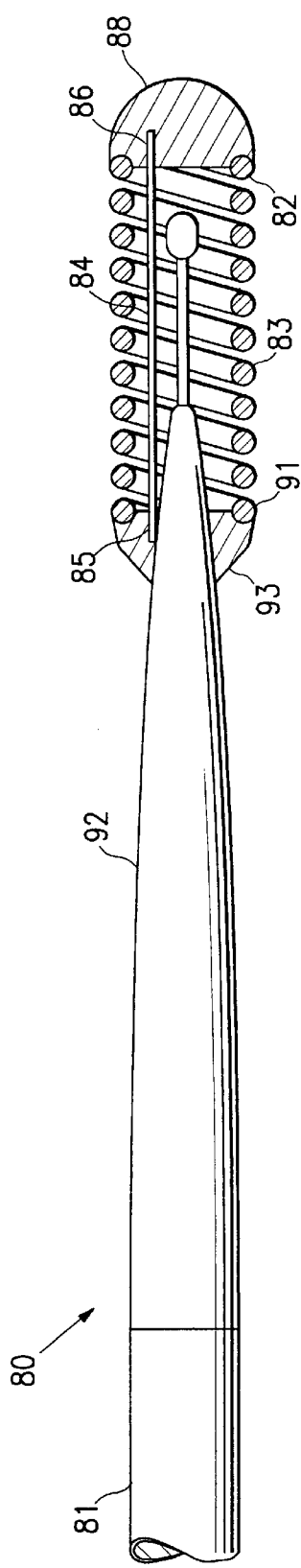
FIG. 9
FIG. 10

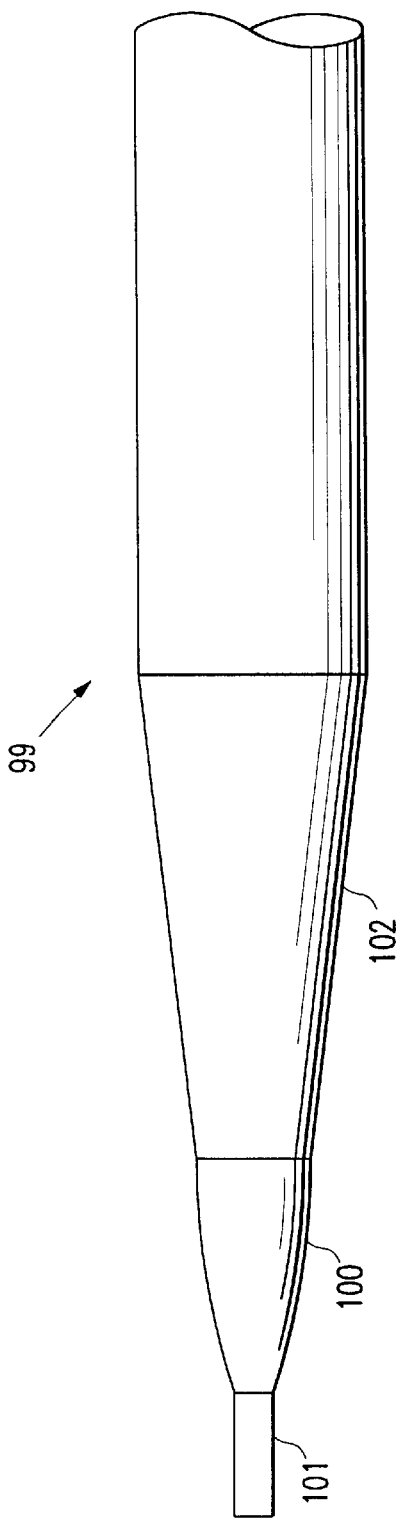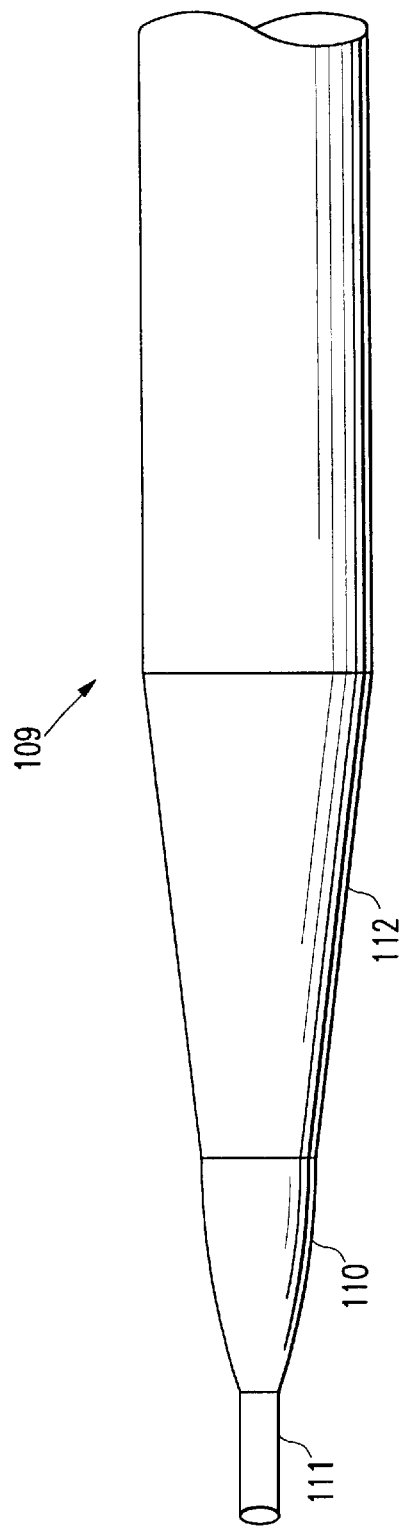

GUIDEWIRE HAVING LINEAR CHANGE IN STIFFNESS

RELATED APPLICATIONS

This application is a continuation in part of co-pending application Ser. No. 08/868,764, filed Jun. 4, 1997, which is incorporated herein in its entirety.

BACKGROUND OF THE INVENTION

This invention relates to the field of guidewires for advancing intraluminal devices such as stent delivery catheters, balloon dilatation catheters, atherectomy catheters and the like within body lumens.

In a typical coronary procedure a guiding catheter having a preformed distal tip is percutaneously introduced into a patient's peripheral artery, e.g. femoral or brachial artery, by means of a conventional Seldinger technique and advanced therein until the distal tip of the guiding catheter is seated in the ostium of a desired coronary artery. There are two basic techniques for advancing a guidewire into the desired location within the patient's coronary anatomy, the first is a preload technique which is used primarily for over-the-wire (OTW) devices and the bare wire technique which is used primarily for rail type systems. With the preload technique, a guidewire is positioned within an inner lumen of an OTW device such as a dilatation catheter or stent delivery catheter with the distal tip of the guidewire just proximal to the distal tip of the catheter and then both are advanced through the guiding catheter to the distal end thereof. The guidewire is first advanced out of the distal end of the guiding catheter into the patient's coronary vasculature until the distal end of the guidewire crosses the arterial location where the interventional procedure is to be performed, e.g. a lesion to be dilated or a dilated region where a stent is to be deployed. The catheter, which is slidably mounted onto the guidewire, is advanced out of the guiding catheter into the patient's coronary anatomy over the previously introduced guidewire until the operative portion of the intravascular device, e.g. the balloon of a dilatation or a stent delivery catheter, is properly positioned across the arterial location. Once the catheter is in position with the operative means located within the desired arterial location, the interventional procedure is performed. The catheter can then be removed from the patient over the guidewire. Usually, the guidewire is left in place for a period of time after the procedure is completed to ensure reaccess to the arterial location is it is necessary. For example, in the event of arterial blockage due to dissected lining collapse, a rapid exchange type perfusion balloon catheter such as described and claimed in U.S. Pat. No. 5,516,336 (McInnes et al), can be advanced over the in-place guidewire so that the balloon can be inflated to open up the arterial passageway and allow blood to perfuse through the distal section of the catheter to a distal location until the dissection is reattached to the arterial wall by natural healing.

With the bare wire technique, the guidewire is first advanced by itself through the guiding catheter until the distal tip of the guidewire extends beyond the arterial location where the procedure is to be performed. Then a rail type catheter, such as described in U.S. Pat. No. 5,061,395 (Yock) and the previously discussed McInnes et al. which are incorporated herein by reference, is mounted onto the proximal portion of the guidewire which extends out of the proximal end of the guiding catheter which is outside of the patient. The catheter is advanced over the catheter, while the position of the guidewire is fixed, until the operative means on the rail type catheter is disposed within the arterial location where the procedure is to be performed. After the procedure the intravascular device may be withdrawn from the patient over the guidewire or the guidewire advanced further within the coronary anatomy for an additional procedure.

Conventional guidewires for angioplasty, stent delivery, atherectomy and other vascular procedures usually comprise an elongated core member with one or more tapered sections near the distal end thereof and a flexible body such as a helical coil or a tubular body of polymeric material disposed about the distal portion of the core member. A shapable member, which may be the distal extremity of the core member or a separate shaping ribbon which is secured to the distal extremity of the core member extends through the flexible body and is secured to the distal end of the flexible body by soldering, brazing or welding which forms a rounded distal tip. Torquing means are provided on the proximal end of the core member to rotate, and thereby steer, the guidewire while it is being advanced through a patient's vascular system.

Further details of guidewires, and devices associated therewith for various interventional procedures can be found in U.S. Pat. No. 4,748,986 (Morrison et al.); U.S. Pat. No. 4,538,622 (Samson et al.): U.S. Pat. No. 5,135,503 (Abrams); U.S. Pat. No. 5,341,818 (Abrams et al.); U.S. Pat. No. 5,345,945 (Hodgson, et al.) and U.S. Pat. No. 5,636,641 (Fariabi) which are hereby incorporated herein in their entirety by reference thereto.

For certain procedures, such as when delivering stents around challenging take-off, e.g. a shepherd's crook, tortuosities or severe angulation, substantially more support and/or vessel straightening is frequently needed from the guidewire than normal guidewires can provide. Guidewires have been commercially introduced for such procedures which provide improved distal support over conventional guidewires, but such guidewires are not very steerable and in some instances are so stiff that they can damage vessel linings when advanced therethrough. What has been needed and heretofore unavailable is a guidewire which provides a high level of distal support with acceptable steerability and little risk of damage when advanced through a patient's vasculature.

In addition, conventional guidewires using tapered distal core sections as discussed above can be difficult to use in many clinical circumstances because they have an abrupt stiffness change along the length of the guidewire, particularly where the tapered portion begins and ends. As a guidewire having a core with an abrupt change in stiffness is moved through tortuous vasculature of a patient, the physician moving the guidewire can feel the abrupt resistance as the stiffness change is deflected by the curvature of the patient's vasculature. The abrupt change in resistance felt by the physician can hinder the physician's ability to safely and controllably advance the guidewire through the vasculature. What has been needed is a guidewire, and particularly a guidewire core member, that does not have an abrupt change in stiffness, particularly in the portions of the distal section that are subject to bending in the vasculature and guiding catheter. The present invention satisfies these and other needs.

SUMMARY OF THE INVENTION

The present invention is directed to an improved guiding device providing enhanced distal support while having a flexible distal tip to provide acceptable steerability and little risk of damage to vessel or chamber linings when advanced through a patient's body lumen such as veins and arteries.

The guiding member of the present invention has an elongated core member with proximal and distal core sections and a flexible tubular body such as a helical coil disposed about and secured to the distal section of the core member. The distal core section has a plurality of distally tapering contiguous core segments having tapers of up to 25° and lengths of up to 15 cm. As used herein the measurement of tapers is the angle of a line tangent to the surface of the segment in line with the longitudinal axis of the core member. The first tapered core segment, which typically has a circular transverse cross-section, preferably tapers from the diameter of the adjacent proximal core section to a diameter of about half to about three quarters of the diameter of the adjacent proximal core section. The second tapered core segment, which also has a circular transverse cross-section, tapers from the smallest diameter of the first tapered core segment to a diameter of not more than one-half the smallest diameter of the first tapered core segment.

One presently preferred embodiment includes a first core segment with a taper in the distal direction and a distally contiguous second core segment having a taper in the distal direction greater than the taper of the first core segment. The taper of the first or proximal segment generally can be up to about 5°, preferably about 0.01° to about 1°, more preferably about 0.011° to about 0.2°. The taper of the second or distal core segment can be up to about 6°, preferably about 0.01° to about 1.1°, more preferably about 0.015° to about 0.45°.

In another presently preferred embodiment, the second tapered core segment has a length greater than the first tapered core segment with the distal segment generally ranging about 1 to about 12 cm, preferably about 2 to about 10 cm and the distal segment generally about 1 to about 8 cm, preferably about 2 to about 6 cm. The tapered core segments may have circular transverse cross-sections and straight exterior surfaces, e.g. frusto-conical shape. However, other shapes are contemplated, e.g. curved exterior surfaces. Indeed, the taper of the contiguous core segments may have a continuously changing taper over all or part of both core segments.

The flexible tubular body such as a helical coil is secured by its distal end to the distal tip of the distal core section or to the distal tip of a shaping ribbon secured to the distal core section in a conventional fashion. The helical coil may be secured by its distal end by soldering, brazing or welding to form a rounded distal tip to the guiding member as done with commercially available guidewire for procedures within a patient's coronary artery.

In one presently preferred embodiment of the invention, the guidewire has an elongated proximal core section having a length of about 65 to about 280 cm and a circular transverse cross-section with a diameter of generally about 0.010 to about 0.035 inch (0.30–0.46 mm), typically about 0.012 to about 0.018 inch (0.30–0.46 mm) for coronary anatomy.

In one presently preferred embodiment of the invention, the second tapered core segment is preferably followed distally with a manually shapable flattened core segment of about 1 to 4 cm in length which preferably has essentially constant transverse dimensions, e.g. 0.001 by 0.003 inch (mm). A helical coil having transverse dimensions about the same as the proximal core section is secured by its distal end to the flattened distal tip of the core member, e.g. solder, and by its proximal end at an intermediate position on the second tapered segment so that the distal end of the second tapered segment resides within the interior of the coil. The coil may have a length of about 2 to about 40 cm or more, but typically will have a length of about 2 to about 10 cm in length.

The guidewire of the invention provides the enhanced distal and proximal support needed for stent deployment, advancement of atherectomy devices and the like and provides a smooth transition between the proximal core section and the flattened distal tip of the core member while exhibiting excellent steerability.

In another aspect of the invention, an intracorporeal device, preferably a guidewire, has an elongated member with at least one longitudinal section having a substantially linear change in stiffness over a length thereof. A substantially linear change in. stiffness of a section of an elongate intracorporeal device may be achieved with an elongate core member having a tapered profile, tapering distally to a smaller transverse dimension and configured to produce a linear change in stiffness. The distal taper of the elongate core may be in the form of a taper having a continuously changing taper angle, i.e. a curvilinear taper profile, or may be achieved by a plurality of tapered segments which are longitudinally short in comparison to the longitudinal length of the tapered section as a whole.

In embodiments where a plurality of tapered segments are used, the tapered segments are preferably contiguous or adjacent each other and have a substantially constant taper angle over the length of each tapered segment. In a preferred embodiment, the taper angle of each tapered segment is greater than the taper angle of the segment proximally adjacent to it. The taper angle and segment length can be controlled from tapered segment to tapered segment to produce the desired bending characteristics of the longitudinal section of the core member.

A core member may be ground to a profile which is calculated mathematically to produce a linear change in stiffness. A useful formula for generating a substantially linear change in stiffness is $$D_L = \left[\frac{64CL}{E\pi} + D_0^4\right]^{\frac{1}{4}}$$

where $D_L$ is the diameter of an elongate core member at length L from a position of starting diameter $D_O$, E is the modulus of elasticity of the material from which the elongate core member is made, and C is a constant.

This formula may be used to generate smooth continuous profiles, or multiple tapered segments where each individual tapered segment has a substantially constant taper angle. In the latter instance, the taper angle and length of each tapered segment can vary to produce the overall desired effect by having the segmented contour substantially follow the formula above. In a preferred embodiment, the points between two adjacent tapered segments, or transition points, have diameters that substantially follow the formula above for $D_L$. As the number of tapered segments increases, this embodiment gradually approaches the smooth continuous curvilinear embodiment. That is, in the limiting case where the number of tapered segments is large, there is little or no difference in stiffness between the segmented core and the smooth curvilinear profile core.

Another approach to generating linear stiffness change in an elongate intracorporeal involves controlling the moment of inertia at any given point in a longitudinal section. A useful formula for such an approach is $$I_L = \frac{CL}{E} + I_0$$

where $I_L$ is the moment of inertia of the elongate core member at length L from a position of starting inertia $I_O$, E is the modulus of elasticity of the core material, and C is a constant that is derived from the boundary conditions of the longitudinal section, specifically, a desired starting moment of inertia, finish moment of inertia, length of section of linear change in stiffness.

A core member with a linear change in stiffness over its length provides improved advancement and control of the distal end of an intracorporeal device through a patient's body lumen. The improvement in handling characteristics results in part from the absence of abrupt changes in flexibility that can obscure the tactile feedback to the physician holding the proximal end of the device. In addition, the abrupt changes in stiffness can cause the device to resist smooth and controllable advancement because a step or threshold force must be applied to overcome the abrupt change in stiffness.

These and other advantages of the invention will become more apparent from the following detailed description of the invention when taken in conjunction with the accompanying exemplary drawings.

BRIEF DESCRIPTION OF THE DRAWINGS

FIG. 1 is an elevational view partially in section of a guidewire embodying features of the invention.

FIG. 2 is a transverse cross-sectional view of the guidewire shown in FIG. 1 taken along the lines 2—2.

FIG. 3 is a transverse cross-sectional view of the guidewire shown in FIG. 1 taken along the lines 3—3.

FIG. 4 is an enlarged view of the distal portion of the guidewire shown in FIG. 1 which indicates the tapers of the distal core section.

FIG. 5 is a partial elevational view of the distal core section of an alternative embodiment of the invention which has a separate shaping ribbon extending from the distal extremity of the core member to the distal end of the coil.

FIG. 6 is an elevational view of a portion of a guidewire having features of the invention.

FIG. 7 is a transverse cross sectional view of the guidewire of FIG. 6 taken at lines 7—7 of FIG. 6.

FIG. 8 is a transverse cross sectional view of the guidewire of FIG. 6 taken at lines 8—8 of FIG. 6.

FIG. 9 is an elevational view of a portion of a guidewire having features of the invention in partial section.

FIG. 10 is an elevational view in partial section of a portion of a guidewire having features of the invention.

FIG. 16 is an elevational view of a section of a guidewire having features of the invention.

FIG. 17 is an elevational view of a section of a guidewire having features of the invention.

DETAILED DESCRIPTION OF THE INVENTION

Figure 11:
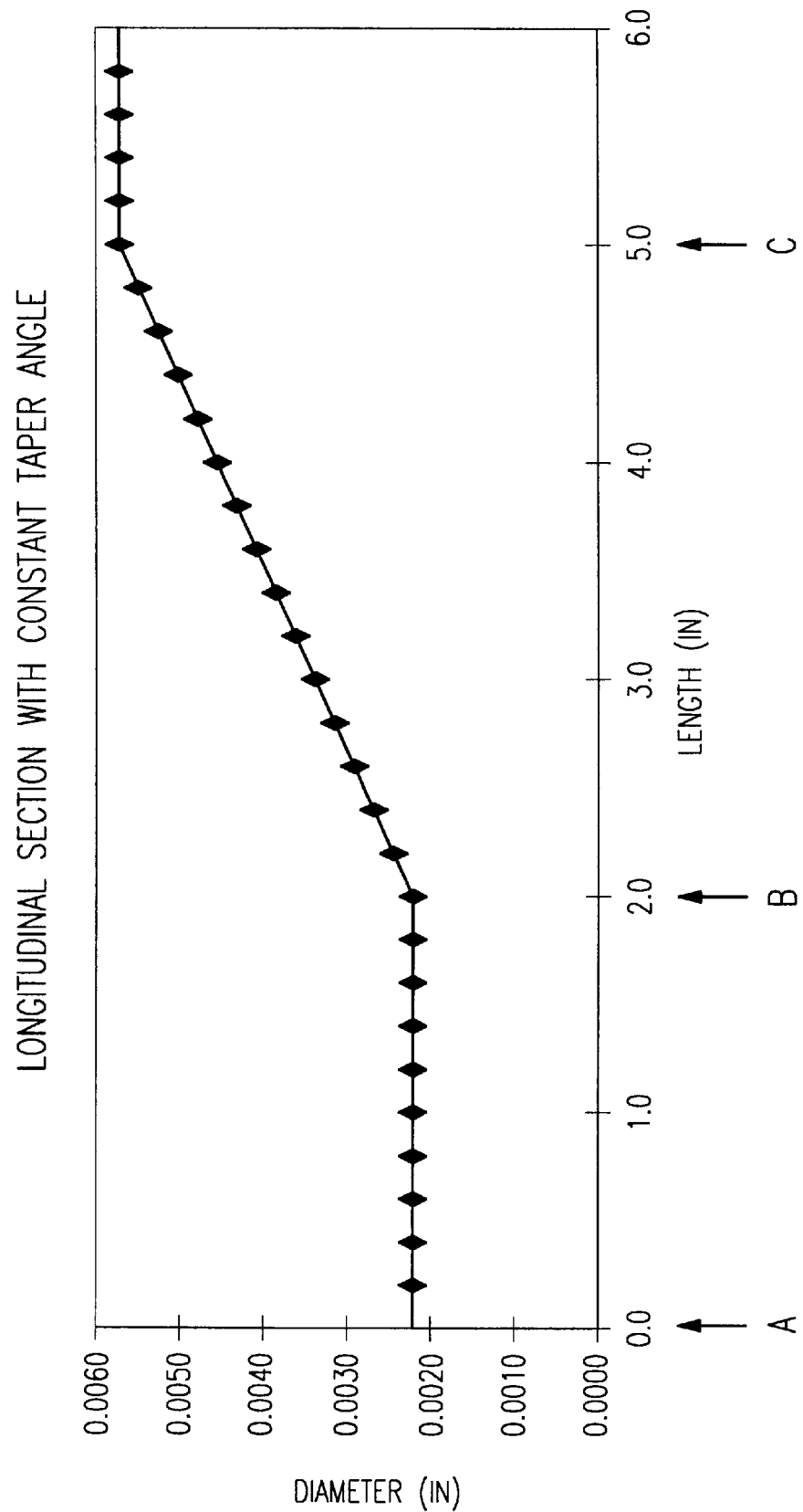
FIG. 11 is a graphic depiction of the diameter of a typical guidewire core member versus the axial position or length from a fixed reference point of that diameter along the core member.

FIGS. 1–3 depict a guidewire 10 which is a presently preferred embodiment thereof which has a core member 11 with a proximal core section 12, a distal core section 13 and a helical coil 14. The distal core section 12 has a first tapered segment 15 and a second tapered core segment 16 which is distally contiguous to the first tapered core segment. The second tapered segment 16 tapers at a greater degree than the first tapered segment and this additional taper provides a much smoother transition when the distal portion of the guidewire 10 is advanced through a tortuous passageway. The degree of taper of the first tapered core segment 15, i.e. the angle between the longitudinal axis 17 and a line tangent to the first tapered core segment 15 is about 2° to about 10°, whereas the taper of the second tapered core segment 16, i.e. the angle between the longitudinal axis and the second tapered core segment is larger than the first angle and is about 5° to about 10° such as is shown in the enlarged view of the guidewire 10 in FIG. 4. While only two tapered core segments are shown in the drawings, any number of tapered core segments can be employed. Moreover, all of a multiple of tapered core segments need not have increasing degrees of tapers in distal direction. However, two or more contiguous tapered core segments over a length of about 5 to 15 cm should have distally increasing degrees of tapering.

Typically, the first tapered segment is about b 3cm in length and the second tapered segment is about 4 cm in length. In a presently preferred embodiment, the guidewire 10 has a proximal core section 12 of about 0.014 inch (0.36 mm) in diameter, the first tapered core segment has a diameter ranging from 0.014 inch down to about 0.008 inch (0.36–0.20 mm) and the second tapered core segment has a diameter ranging from about 0.008 to about 0.002 inch (0.20–0.05 mm). A flattened distal tip 18 extends from the distal end of the second tapered core segment 16 to the body of solder 20 which secures the distal tip 18 of the core member 11 to the distal end of the helical coil 14. A body of solder 21 secures the proximal end of the helical coil 14 to an intermediate location on the second tapered segment 16.

The core member 11 is coated with a lubricious coating 19 such as a fluoropolymer, e.g. TEFLON® available from DuPont, which extends the length of the proximal core section 12. The distal section 13 is also provided a lubricous coating, not shown for purposes of clarity, such as a MICROGLIDE™ coating used by the present assignee, Advanced Cardiovascular Systems, Inc. on many of its commercially available guidewires. Hydrophilic coating may also be employed.

The core member may be formed of stainless steel, NiTi alloys or combinations thereof such as described in U.S. Pat. No. 5,341,818 (Abrams et al) which has been incorporated herein. Other materials such as the high strength alloys described in U.S. Pat. No. 5,636,641 (Fariabi), which has also been incorporated herein by reference, may also be used.

The helical coil 14 is formed of a suitable radiopaque material such as platinum or alloys thereof or formed of other material such as stainless steel and coated with a radiopaque material such as gold. The wire from which the coil is made generally has a transverse diameter of about 0.003 inch (0.05 mm). The overall length of the coil 14 is typically about 3 cm. Multiple turns of the distal portion of coil 14 may be expanded to provide additional flexibility.

In an alternative embodiment shown in FIG. 5, the flattened distal segment of the core member shown in FIG. 1 is replaced with a shaping ribbon 30 which is secured by its distal end to the distal end of the coil 14 and by its proximal end to the distal extremity of the core member 11.

While the specific embodiments described above are directed to tapered segments with constant tapers along their lengths, the taper need not be constant. For example, the tapers of contiguous core segments may be gradually increasing in the distal direction, with the taper, i.e. a tangent line, crossing the junction between the two adjacent tapers being a continuous function. Guidewires are generally about 90 to about 300 cm in length, and most commercially available guidewires for the coronary anatomy are either 175 cm or 190 cm in length.

Multiple tapers may be ground simultaneously or as separate operations. A centerless grinder with profile capabilities may be used to grind the tapers simultaneously. A manual centerless grinding may be employed to create separate tapers in separate operations. Tapers may also be formed by other means such as chemical means, e.g. etching, or laser means.

Another aspect of the invention can be seen in FIG. 6 which is a distal portion of an intracorporeal device in the form of a guidewire 40. The guidewire 40 has an elongated core member 41, with a longitudinal section 42, the longitudinal section having a substantially linear change in stiffness along its length 43. The length 43 of the longitudinal section can be up to 60 cm, preferably about 5 to about 35 cm, more preferably about 10 to about 25 cm. The longitudinal section 42 tapers distally to a smaller transverse dimension or diameter to a more flexible distal segment. A flexible body 44 having a proximal end 45 and a distal end 46 is secured at its distal end 46 to a distal end 47 of a distal segment 48 of the elongate core member 41 by a first body of solder 51. The proximal end 45 of the flexible body 44 is secured to the longitudinal section 42 of the elongate core member by a second body of solder 52.

The longitudinal section 42, and preferably the entire elongate core member 41 of the guidewire 40 is made from high tensile stainless steel, or hi-ten 304 stainless steel. The longitudinal section 42 can also be made from other high strength metals, some of which are precipitation hardenable, including 304 stainless steel, MP35N, L605. The longitudinal section 42 may also be made from pseudoelastic alloys, such as NiTi. The longitudinal section 42 has a curvilinear profile with a smooth continuous change in taper angle over its length 43. The curvilinear profile of the longitudinal section 42 preferably substantially follows the formula $$D_L = \left[\frac{64CL}{E\pi} + D_0^4\right]^{\frac{1}{4}}$$

where $D_L$ is the diameter of the longitudinal section at length L from a position of starting diameter $D_O$, E is the modulus of elasticity of the core member material, and C is a constant that is determined by the boundary conditions of the longitudinal section.

The constant C is determined by the boundary conditions of a desired section using the equation $$C = \frac{\pi E(D_L^4 - D_0^4)}{64L}$$

where a desired starting diameter $D_O$, finish diameter $D_L$, length of the section having a linear change in stiffness L, and modulus of elasticity E of the section material are inserted into the equation which is then solved for C.

A typical modulus of elasticity for 304 stainless steel is approximately 28×10⁶ psi. An example of a set of values for a longitudinal section 42 having features of the invention are 0.002 inches for a starting diameter $D_O$, 0.013 inches for a finish or ending diameter $D_L$, 20 cm for the length of the longitudinal section L, and 28×10⁶ psi for the modulus of elasticity of the core member E. Solving for C yields a constant value of about 0.005 pound-inches. Another example of a set of values for a longitudinal section 42 having features of the invention are 0.0025 inches for a starting diameter $D_O$, 0.0076 inches for a finish or ending diameter $D_L$, 25 cm for the length of the longitudinal section L, and 30×10⁶ psi for the modulus of elasticity of the core member E. Solving for C yields a constant value of about 0.00049 pound-inches.

Another more generalized approach for achieving a substantially linear change in stiffness in a longitudinal section 42 or elongate core member 41 is to vary the moment of inertia along the longitudinal section according to the formula $$I_L = \frac{CL}{E} + I_0$$

where $I_L$ is the moment of inertia of the elongate core member at length L from a position of starting inertia $I_O$, E is the modulus of elasticity of the core material, and C is a constant that is derived from the boundary conditions of the longitudinal section. The constant C is determined by inserting the values of a desired starting moment of inertia $I_O$, finish moment of inertia $I_L$, length of section of linear change in stiffness L, and modulus of elasticity E into the equation and solving for C.

The moment of inertia of a point on a longitudinal section 42 or elongate core member 41 can be varied by controlling the diameter in a round cross section as discussed above. Other variations in transverse cross section shape and configuration can be made in embodiments having non-round transverse cross sections. Finally, because bending stiffness is equal to the modulus of elasticity multiplied by the moment of inertia, the bending stiffness may be controlled by adjusting the modulus of elasticity along the length of a longitudinal section 42 or elongate core member 41.

FIG. 7 is a transverse cross sectional view of the guidewire 40 of FIG. 6 taken at lines 7—7 of FIG. 6. The elongated core member 41 preferably has a round cross section. The core member 41 may optionally be coated with a lubricious coating 53. The coating 53 is preferably a hydrophyllic polymer, but may also be made of polymers such as TFE or the like. FIG. 8 is a transverse cross sectional view of the guidewire 40 in FIG. 6 taken at lines 8—8 of FIG. 6. The flexible body 44 is in the form of a helical coil which is disposed about the distal segment 48 of the elongate core member 41. The distal segment 48 of the elongate core member is flattened to improve shapability of the distal segment.

FIG. 9 is an elevational view of a guidewire 60 having features of the invention. The guidewire 60 has an elongated core member 61 with a longitudinal section 62 having a plurality of tapered segments 63 tapering distally to a more flexible distal segment 64. Transition points 65 are disposed between adjacent tapered segments 63. A flexible body member 66 is disposed over the distal segment 64 and a portion of the longitudinal section 62. The flexible body 66 has a proximal end 67 and a distal end 68 with the distal end 68 of the flexible body being secured to a distal end 71 of the distal segment 64 of the elongated core member 61 with a first body of solder 72. The proximal end 67 of the flexible body 66 is secured to the longitudinal section 62 with a second body of solder 73. In a preferred embodiment, each tapered segment 63 of the longitudinal section 62 has a substantially constant taper angle with the taper angle of each tapered segment being greater than the tapered segment proximally adjacent thereto. Preferably, the diameter of the longitudinal section 62 at the transition points 65 or alternatively midpoints 74 of the tapered segments substantially follows the formula $$D_L = \left[\frac{64CL}{E\pi} + D_0^4\right]^{\frac{1}{4}}$$

where $D_L$ is the diameter of the longitudinal section at a transition point at length L from a position of starting diameter $D_O$, E is the modulus of elasticity of the core member material, and C is a constant that is determined by the boundary conditions of the longitudinal section. The determination of the constant C is performed in a manner similar to the determination of the constant C discussed above with regard to the embodiment of FIG. 6. The tapered segments 63 of the longitudinal section 62 or core member 61 can be up to 10 inches in length, preferably about 0.1 to about 5 inches in length, more preferably about 0.25 to about 3 inches in length.

FIG. 10 is an elevational view of a guidewire 80 having features of the invention. The guidewire 80 is similar to the guidewire 40 of FIG. 6 except that the elongate core member 81 does not extend to a distal end 82 of a flexible body 83. Instead, a shaping ribbon 84 having a proximal end 85 and a distal end 86 has its distal end 86 secured to the distal end 82 of the flexible body 83 with a first body of solder 88. A proximal end 91 of the flexible body 83 and the proximal end 85 of the shaping ribbon 84 are secured to a longitudinal section 92 with a second body of solder 93. The guidewire 80 has a longitudinal section 92 configured to produce a substantially linear change in bending stiffness similar to the longitudinal section 42 of FIG. 6.

FIG. 11 is a graph of values determined for a typical guidewire core member with diameter in inches along the vertical axis and length or axial distance from a starting point on the core member in inches along the horizontal axis. At the starting point A of the graph, the diameter of the core member is approximately 0.0022 inches. Point A represents the core at a distal end of a distal segment. The distal segment of the core member continues proximally until the distal end of the tapered longitudinal section of the elongate core is reached, which is represented by point B on the graph. Moving proximally from the junction of the distal segment and the tapered longitudinal section, the diameter of the core member increases proportionally with a length from the junction. This type of tapered longitudinal section is representative of a typical tapered guidewire section having a constant taper angle over the length of the section. The taper diameter increases proximally until the junction between the tapered longitudinal section meets the constant diameter section of the elongate core which is represented by point C on the graph.

Figure 12:
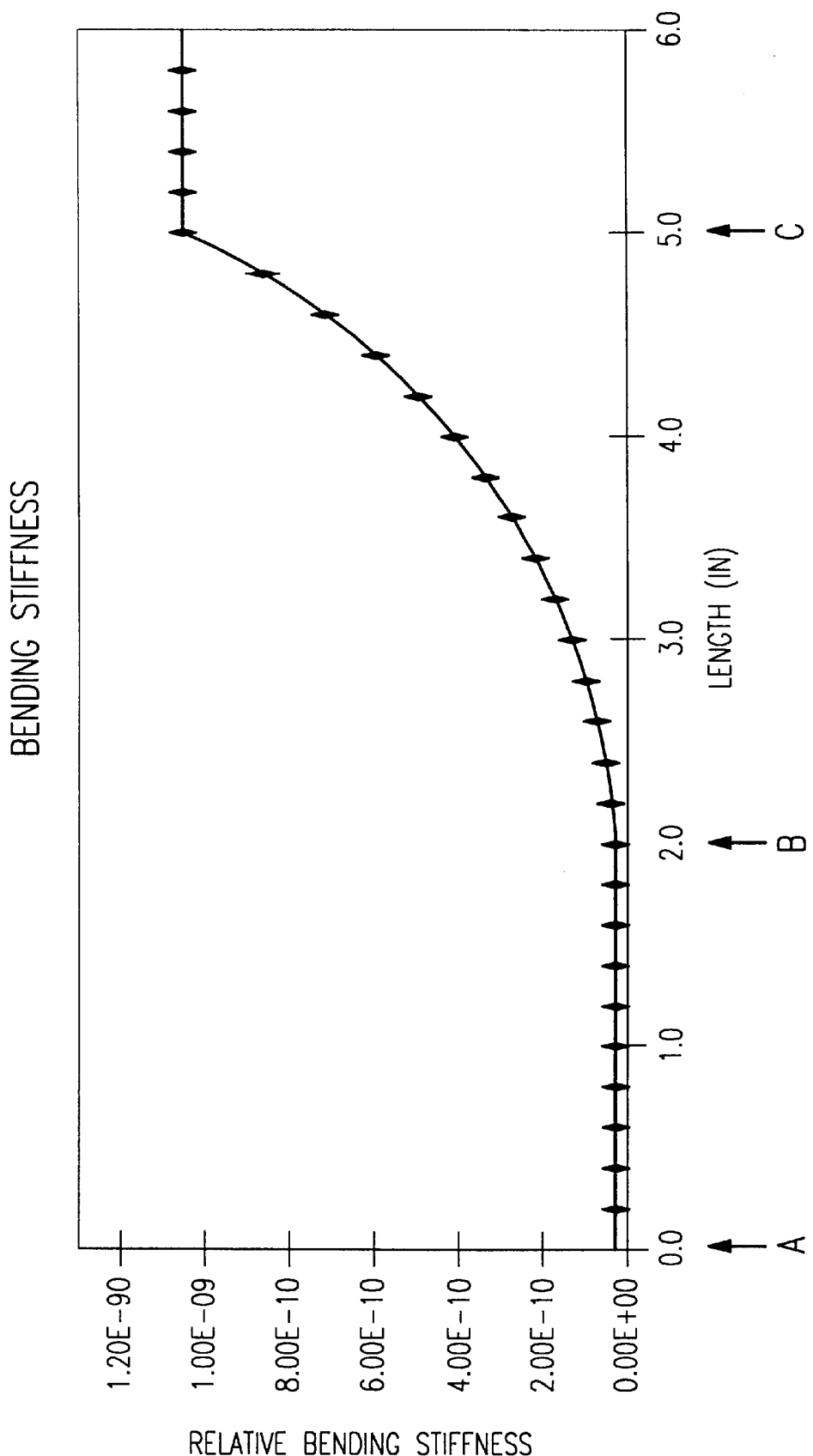
FIG. 12 is a graphic depiction of relative bending stiffness values of a typical guidewire core member versus length from a reference point along the core member.

FIG. 12 is a graph of relative bending stiffness values of the elongate core member of FIG. 11 along its axial length. As can be seen from the graph of FIG. 12, the plot of bending stiffness of the tapered longitudinal section starting at point B and proceeding proximally to point C is not a straight line. There is a curvature to the plot which becomes progressively steeper as point C is approached. Near point C, the plot becomes quite steep, which represents an abrupt change in bending stiffness in the vicinity of point C.

Figure 13:
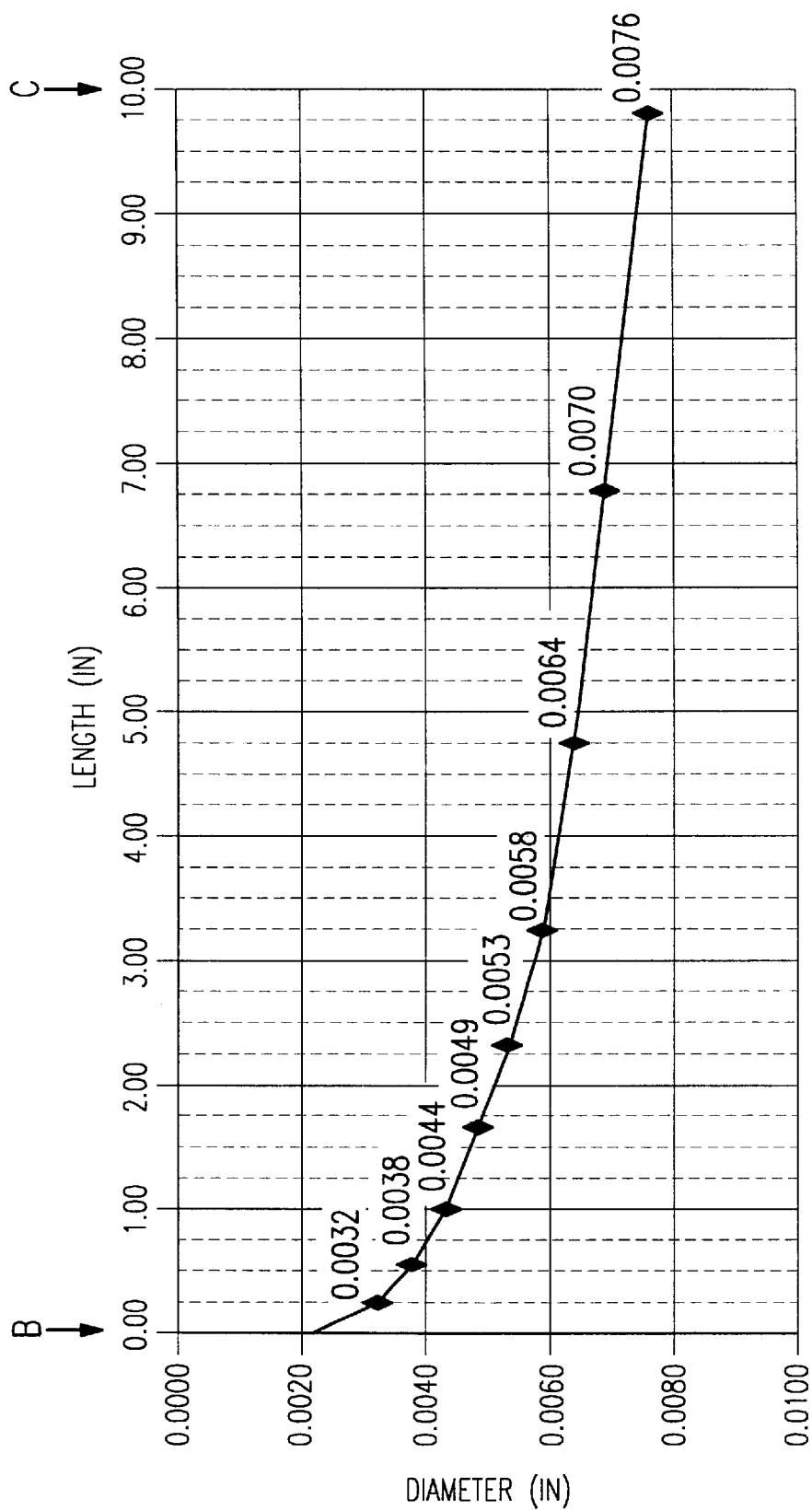
FIG. 13 is a graphic depiction of the diameter of a typical guidewire core member versus the length from a fixed reference point or longitudinal position of that diameter.

FIG. 13 is a plot or graph of the diameter of a guidewire core versus the axial position of the diameter in a core having a longitudinal section with a substantially linear change in bending stiffness. The graph begins at point B at length 0 with the core member having a diameter of about 0.002 inches. Point B of FIG. 13 has a similar starting diameter to point B in FIG. 11. FIG. 13 is representative a graph of stiffness values for an embodiment of the invention having a plurality of tapered segments, with each tapered segment having a substantially constant taper angle. The change in diameter or taper angle of the tapered segments is greater at the distal end of the longitudinal section and decreases proximally. The slope of the graph or taper angle for each tapered segment is less than that of the tapered segment that is distally adjacent. The profile of transition points between each pair of adjacent tapered segments of the longitudinal section depicted by the graph of FIG. 13 substantially follows the formula $$D_L = \left[\frac{64CL}{E\pi} + D_0^4\right]^{\frac{1}{4}}$$

where $D_L$ is the diameter of the longitudinal section at a transition point at length L from a position of starting diameter $D_O$, E is the modulus of elasticity of the core member material, and C is a constant that is determined by the boundary conditions of the longitudinal section.

Figure 14:
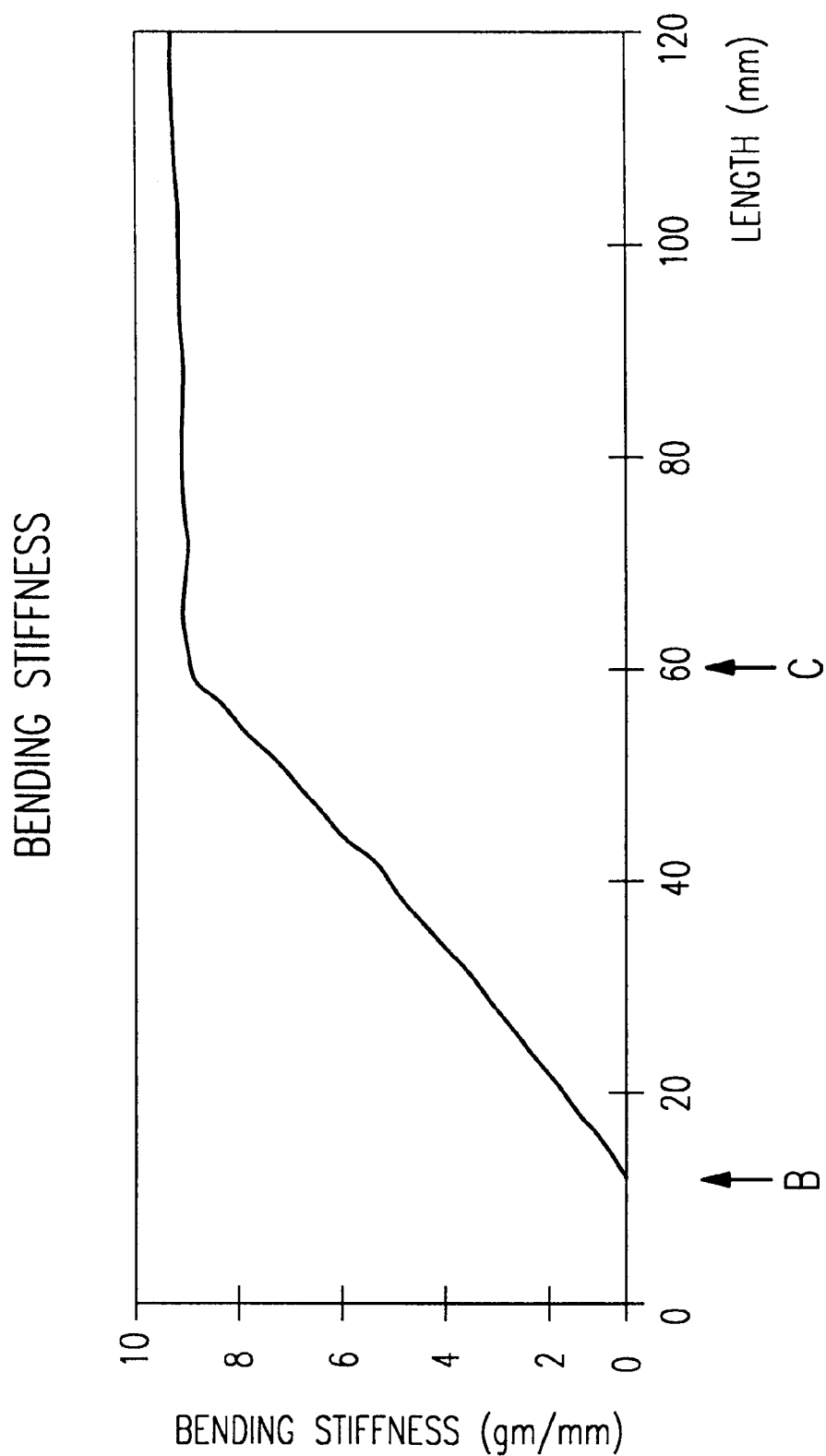
FIG. 14 is a graphic depiction of relative stiffness values of a typical guidewire core member versus longitudinal position or length along the core member.

FIG. 14 depicts typical relative bending stiffness values of a core member versus axial or longitudinal position along the length of the core member. The core member has a longitudinal section with a taper profile configured to generate a linear change in bending stiffness. The plot from point B to point C does not change appreciably in slope which indicates a constant change in stiffness over that section. This graph is not indicative of the progressively steeper slope found on the stiffness curve of FIG. 12 where an abrupt change in stiffness is noted at point C, in addition to other points.

Bending stiffness can be measured in a variety of ways. Typical methods of measuring bending stiffness include extending a portion of the sample to be tested from a fixed block with the sample immovably secured to the fixed block and measuring the amount of force necessary to deflect the end of the sample that is away from the fixed block a predetermined distance. A similar approach can be used by fixing two points along the length of a sample and measuring the force required to deflect the middle of the sample a fixed amount. Those skilled in the art will realize that a large number of variations on these basic methods exist including measuring the amount of deflection that results from a fixed amount of force on the free end of a sample, and the like. Although the graph of FIG. 14 shows relative bending stiffness in terms of grams per millimeter, the values shown were derived from a specific test apparatus using the methods discussed above. Other methods of measuring bending stiffness may produce values in different units of different overall magnitude, however, it is believed that the overall shape of the graph will remain the same regardless of the method used to measure bending stiffness.

Figure 15:
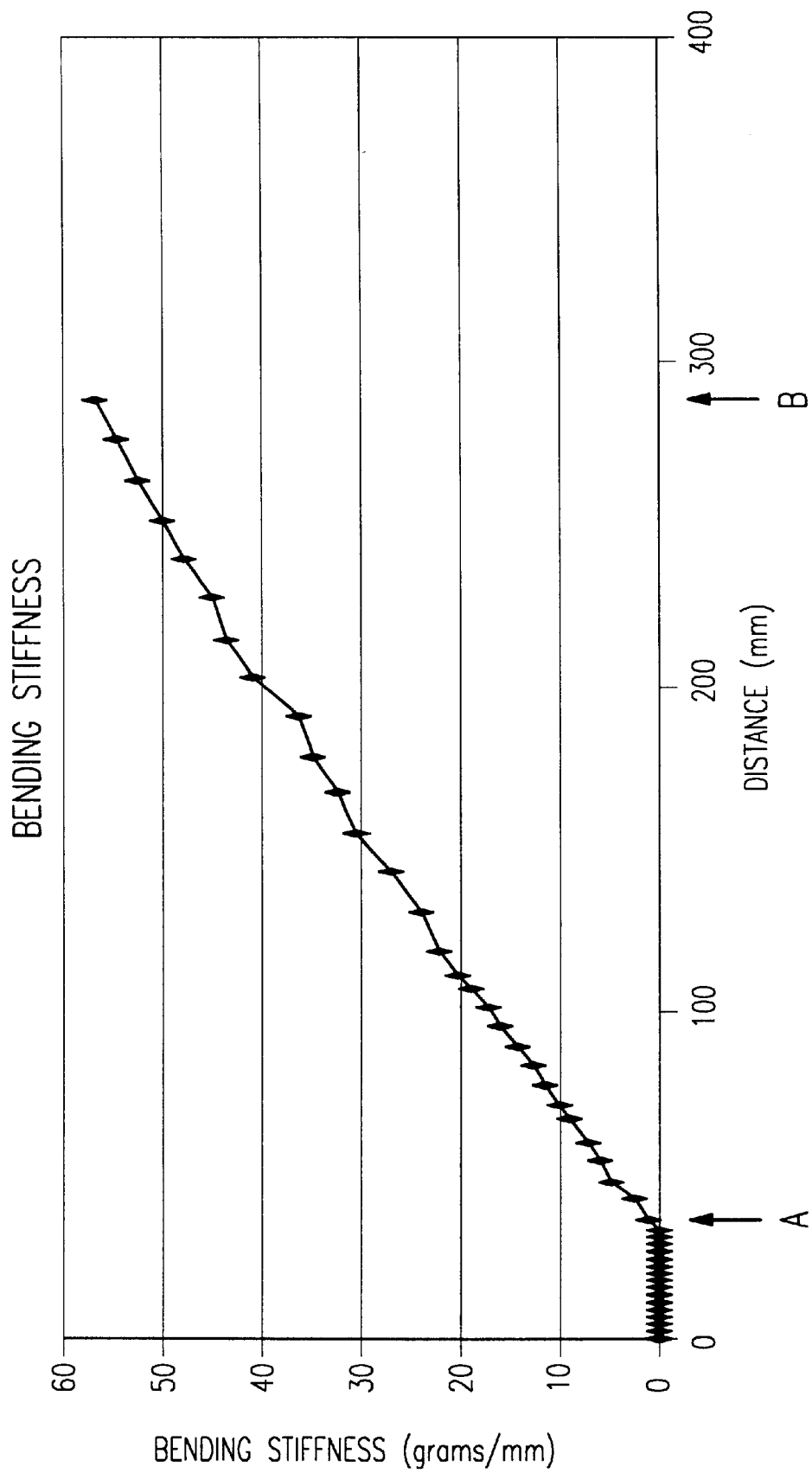
FIG. 15 is a graphic depiction of relative stiffness values of a typical guidewire core member versus longitudinal position or length along the core member.

FIG. 15 depicts typical relative bending stiffness values of a longitudinal section of another embodiment of a core member versus axial position along the core member. The slope of the graph from point A to point B is essentially constant, indicating a substantially constant change in bending stiffness from point A to point B.

Unless otherwise described herein, conventional materials and manufacturing methods may be used to make the guiding members of the present invention. Additionally, various modifications may be made to the present invention without departing from the scope thereof.

It may be desirable to have multiple tapered longitudinal sections or sections having a varied flexibility. Any combination of multiple longitudinal sections may be used including sections having a substantially constant taper angle, sections having a substantially linear change in stiffness along a length thereof, or sections of substantially constant diameter along a length thereof. In FIG. 16, a preferred embodiment of an elongate core member 99 has a longitudinal section 100 of substantially linear change in stiffness intermediate to a distal segment 101 having a substantially constant diameter and a constant taper section 102 with a constant taper angle increasing in diameter proximally. The distal segment 101 has a diameter of about 0.002 to about 0.003 inches, and a length of about 3 to about 6 cm. The longitudinal section 100 having a substantially linear change in stiffness is about 15 to about 25 cm in length and tapers to an increased diameter proximally from about 0.002 to about 0.003 inches at a distal end to about 0.0065 to about 0.0085 inches at a proximal end. The constant taper section 102 tapers proximally from a diameter of about 0.0065 to about 0.0085 inches at its distal end to an increased diameter of about 0.012 to about 0.014 inches at its proximal end.

In FIG. 17, an embodiment of an elongate core member 109 has a longitudinal section 110 of substantially linear change in stiffness intermediate to a more flexible proximal portion 111 having a substantially constant diameter and a constant taper section 112 with a constant taper angle increasing in diameter.

What is claimed is:

1. An intracorporeal device comprising an elongated member having a substantially linear change in stiffness over a longitudinal length thereof.

2. The device of claim 1 wherein the length of the elongated member has a continuously changing taper angle producing a curvilinear profile that is configured to produce the substantially linear change in stiffness over said length.

3. The device of claim 1 wherein the elongated member has a plurality of tapered segments configured to produce the substantially linear change in stiffness over the length of the member.

4. The device of claim 3 wherein each tapered segment has a substantially constant taper angle.

5. The device of claim 3 wherein the elongate core member comprises at least 3 to about 100 tapered segments.

6. The device of claim 3 wherein the elongate core member comprises about 5 to about 20 tapered segments.

7. The device of claim 1 wherein the elongated core member comprises a material with changing hardness in a longitudinal direction configured such that the change in hardness produces a substantially linear change in stiffness along the length of the core member.

8. The device of claim 1 wherein the elongated member is about 1 to about 50 cm in length.

9. The device of claim 1 wherein the elongated member is about 10 to about 25 cm in length.

10. The device of claim 1 wherein the elongated member tapers distally to a more flexible distal portion.

11. A guidewire comprising an elongate core member with at least one longitudinal section having a substantially linear change in stiffness over a length thereof.

12. The guidewire of claim 11 wherein the longitudinal section of the elongate core member has a continuously changing taper angle yielding a curvilinear profile configured to produce a substantially linear change in stiffness over the length of the longitudinal section.

13. The guidewire of claim 11 wherein the longitudinal section of the elongate core member has a plurality of tapered segments.

14. The guidewire of claim 13 wherein each tapered segment has a substantially constant taper angle with the tapered segments being configured to produce a substantially linear change in stiffness over the length of the section.

15. The guidewire of claim 13 wherein the elongate core member of the longitudinal section comprises about 3 to about 100 tapered segments.

16. The guidewire of claim 13 wherein the elongate core member of the longitudinal section comprises about 5 to about 20 tapered segments.

17. The guidewire of claim 11 wherein the longitudinal section further comprises a material with changing hardness in a longitudinal direction configured such that the change in hardness produces a substantially linear change in stiffness along the length of the section.

18. The guidewire of claim 11 wherein the longitudinal section is about 1 to about 50 cm in length.

19. The guidewire of claim 11 wherein the longitudinal section is about 10 to about 25 cm in length.

20. The guidewire of claim 12 wherein the longitudinal section substantially follows the formula $$D_L = \left[\frac{64CL}{E\pi} + D_0^4\right]^{\frac{1}{4}}$$

where $D_L$ is the diameter of the elongate core member at length L from a position of starting diameter $D_O$, E is the modulus of elasticity of the core member material, and C is a constant that depends on the boundary conditions of the longitudinal section.

21. The guidewire of claim 13 wherein the longitudinal section further comprises transition points between adjacent tapered segments and the diameter of the elongate core member at the transition points substantially follows the formula $$D_L = \left[\frac{64CL}{E\pi} + D_0^4\right]^{\frac{1}{4}}$$

where $D_L$ is the diameter of the elongate core member at length L from a position of starting diameter $D_O$, E is the modulus of elasticity of the core member material, and C is a constant that depends on the boundary conditions of the longitudinal section.

22. The guidewire of claim 12 wherein the longitudinal section substantially follows the formula $$I_L = \frac{CL}{E} + I_0$$

where $I_L$ is the moment of inertia of the longitudinal section at length L from a position of starting inertia $I_O$, E is the modulus of elasticity of the longitudinal section, and C is a constant that depends on the boundary conditions of the longitudinal section.

23. The guidewire of claim 13 wherein the longitudinal section further comprises transition points disposed between adjacent tapered segments and the moment of inertia of the longitudinal section at the transition points substantially follows the formula $$I_L = \frac{CL}{E} + I_0$$

where $I_L$ is the moment of inertia of the longitudinal section at length L from a position of starting inertia $I_O$, E is the modulus of elasticity of the longitudinal section, and C is a constant that depends on the boundary conditions of the longitudinal section.

24. The guidewire of claim 11 wherein the longitudinal section tapers distally to a more flexible distal portion.

25. The guidewire of claim 11 wherein the longitudinal section tapers proximally to a more flexible proximal portion.

26. The guidewire of claim 11 further comprising a constant taper section of the elongate core member adjacent the longitudinal section.

27. The guidewire of claim 26 wherein the constant taper section is proximally adjacent the longitudinal section.

28. The guidewire of claim 27 further comprising a distal segment having a substantially constant diameter disposed distally adjacent the longitudinal section.

29. A guidewire comprising an elongate core member having at least one longitudinal section with a continuously changing taper angle yielding a curvilinear profile.

30. The guidewire of claim 29 wherein the longitudinal section tapers distally to a reduced transverse dimension.

31. The guidewire of claim 29 wherein the longitudinal section has a length of about 1 to about 100 cm.

32. The guidewire of claim 29 wherein the longitudinal section has a length of about 10 to about 25 cm.

33. An elongated guidewire comprising:
a) an elongated core member having proximal and distal core sections, with the distal core section having a first tapered core segment having an angle of taper and a distally contiguous second tapered core segment which is longer than the first tapered core segment and which has an angle of taper greater than the angle of taper of the first tapered core segment; and
b) a flexible body disposed about and secured to the distal core section.

34. The elongated guidewire of claim 33 wherein the second tapered core segment has an angle of taper of up to about 0.44°.

35. The elongated guidewire of claim 33 wherein the second tapered core segment tapers at about 4° to about 12°.

36. The elongated guidewire of claim 33 wherein the first tapered core segment tapers at about 1° to about 12°.

37. The elongated guidewire of claim 33 wherein the first tapered core segment tapers at about 1° to about 10°.

38. The elongated guidewire of claim 33 wherein each of the first and second tapered core segments extend a length of about 1 to about 15 cm.

39. The elongated guidewire of claim 33 wherein the second tapered core segment is longer than the first tapered core segment.

40. The elongated guidewire of claim 33 wherein the first tapered core segment is about 1 to about 8 cm in length.

41. The elongated guidewire of claim 33 wherein the first tapered core segment is about 2 to about 6 cm in length.

42. Te elongated guidewire of claim 33 wherein the second tapered core segment is about 1 to about 12 cm in length.

43. The elongated guidewire of claim 33 wherein the second tapered core segment is about 2 to about 10 cm in length.

44. The elongated guidewire of claim 33 wherein the flexible body is a helical coil with proximal and distal ends.

45. The elongated guidewire of claim 44 wherein the distal end of the helical coil is secured to the distal end of the core member.

46. The elongated guidewire of claim 44 wherein the helical coil has a proximal end secured to an intermediate location on the second tapered core segment.

47. The elongated guidewire of claim 44 wherein a shaping ribbon having proximal and distal extremities is secured by its proximal extremity to the distal end of the core member and by its distal extremity to the distal end of the helical coil.

48. The elongated guiding member of claim 44 wherein the helical coil is about 1.5 to about 40 cm in length.

49. The elongated guide member of claim 33 wherein the first and second tapered core segments have truncated conical shapes.

50. An elongated guidewire which comprises:
a) an elongated core member having a proximal core section and a distal core section with at least two contiguous tapered segments including a tapered proximal segment and a tapered distal segment, the tapered distal segment having a taper angle of up to about 0.44° and greater than the taper of the tapered proximal segment; and
b) a flexible body disposed about and secured to the distal core section.

51. The guidewire of claim 50 wherein the helical coil has a proximal end secured to an intermediate location on the tapered distal segment.

52. The elongated guidewire of claim 50 wherein the tapered distal segment tapers at an angle of at least about 0.029°.

53. The elongated guidewire of claim 50 wherein the distal core section of the elongated core member further comprises a flattened distal segment distal to the tapered distal segment.

54. The elongated guidewire of claim 53 wherein the flexible body is a helical coil which is secured to a distal end of the flattened distal segment.

55. An elongated guidewire which comprises:
   a) an elongated core member having a proximal core section and a distal core section with at least two contiguous tapered segments, a tapered proximal segment and a tapered distal segment having a length greater than the tapered proximal segment and at least about 2 cm; and
   b) a helical coil secured to at least a portion of the distal core section.

56. The elongated guidewire of claim 55 wherein the tapered proximal core segment is about 1 to about 8 cm in length.

57. The elongated guidewire of claim 55 wherein the tapered proximal core segment is about 2 to about 6 cm in length.

58. The elongated guidewire of claim 55 wherein the tapered distal core segment is about 2 to about 12 cm in length.

59. The elongated guidewire of claim 55 wherein the tapered distal core segment is about 2 to about 10 cm in length.

60. An elongated guidewire which comprises:
   a) an elongated core member having a proximal core section and a distal core section, with the distal core section having at least one tapered core segment that has a length of at least about 1 cm and has a continuously changing taper substantially along the entire length of a curved exterior surface; and
   b) a flexible body secured to the distal core section.

61. The guidewire of claim 60 wherein the continuously changing taper increases in a distal direction.

\* \* \* \* \*

UNITED STATES PATENT AND TRADEMARK OFFICE
CERTIFICATE OF CORRECTION

PATENT NO.   : 6,390,993 B1
DATED        : May 21, 2002
INVENTOR(S)  : Wayne E. Cornish et al.

Page 1 of 1

It is certified that error appears in the above-identified patent and that said Letters Patent is hereby corrected as shown below:

<u>Title page,</u>
Item [75], add the following co-inventors:
-- Olin J. Palmer, Redwood City; Kent C. Stalker, Temecula; --.

Signed and Sealed this

Seventeenth Day of February, 2004

JON W. DUDAS
*Acting Director of the United States Patent and Trademark Office*